United States Patent
Morris et al.

(10) Patent No.: US 10,994,259 B2
(45) Date of Patent: May 4, 2021

(54) METAL-ORGANIC FRAMEWORKS FOR THE ADSORPTION AND CATALYTIC TRANSFORMATIONS OF CARBON DIOXIDE

(71) Applicant: VIRGINIA TECH INTELLECTUAL PROPERTIES, INC., Blacksburg, VA (US)

(72) Inventors: Amanda Morris, Blacksburg, VA (US); Jie Zhu, San Diego, CA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 16/545,815

(22) Filed: Aug. 20, 2019

(65) Prior Publication Data
US 2020/0055020 A1    Feb. 20, 2020

Related U.S. Application Data

(60) Provisional application No. 62/719,944, filed on Aug. 20, 2018.

(51) Int. Cl.
| | |
|---|---|
| *B01J 20/22* | (2006.01) |
| *B01J 31/22* | (2006.01) |
| *B01J 35/10* | (2006.01) |
| *B01J 20/28* | (2006.01) |
| *B01D 53/62* | (2006.01) |
| *B01D 53/02* | (2006.01) |
| *C25B 11/04* | (2021.01) |
| *C25B 3/04* | (2006.01) |
| *A61K 49/10* | (2006.01) |
| *C07D 317/38* | (2006.01) |
| *C07D 317/64* | (2006.01) |
| *B01J 31/16* | (2006.01) |

(52) U.S. Cl.
CPC ......... *B01J 20/226* (2013.01); *A61K 49/108* (2013.01); *B01D 53/02* (2013.01); *B01D 53/62* (2013.01); *B01J 20/28061* (2013.01); *B01J 20/28064* (2013.01); *B01J 31/1691* (2013.01); *B01J 31/2239* (2013.01); *B01J 35/1019* (2013.01); *B01J 35/1023* (2013.01); *C07D 317/38* (2013.01); *C07D 317/64* (2013.01); *C25B 3/04* (2013.01); *C25B 11/0447* (2013.01); *B01D 2253/204* (2013.01); *B01D 2257/504* (2013.01); *B01J 2231/34* (2013.01); *B01J 2231/625* (2013.01); *B01J 2531/16* (2013.01); *B01J 2531/38* (2013.01); *B01J 2531/48* (2013.01); *B01J 2531/62* (2013.01); *B01J 2531/821* (2013.01); *B01J 2531/845* (2013.01); *B01J 2531/847* (2013.01)

(58) Field of Classification Search
CPC .. A61K 49/101; A61K 49/106; A61K 49/108; B01J 31/2239; B01J 20/28061; B01J 35/1019; B01J 35/1023; B01J 31/169; B01J 2231/625; B01J 2531/48; B01J 2531/847; B01J 2531/845; B01J 2231/34; B01J 20/226; B01J 20/28064; B01J 2531/62; B01J 2531/38; B01J 2531/16; B01J 2531/821; B01D 53/02; B01D 2257/504; B01D 53/62; B01D 2253/204; C25B 3/04; C25B 11/0447; C07D 317/38; C07D 317/64

See application file for complete search history.

(56) References Cited

U.S. PATENT DOCUMENTS

| | | | |
|---|---|---|---|
| 8,653,292 B2 * | 2/2014 | Hafizovic | C07C 7/12 556/55 |
| 2015/0217268 A1 * | 8/2015 | Farha | B01J 20/3085 95/139 |

OTHER PUBLICATIONS

Zhu et al., J. Am. Chem. Soc., 2018, 140, p. 993-1003. (Year: 2018).*
Xin et al., Transition Met. Chem., 1992, 17, p. 147-154. (Year: 1992).*
Feng et al., JACS, 2013, 135, p. 17105-17110. (Year: 2013).*

* cited by examiner

*Primary Examiner* — Michael G. Hartley
*Assistant Examiner* — Leah H Schlientz
(74) *Attorney, Agent, or Firm* — Innovators Legal

(57) ABSTRACT

Novel crystalline porous materials known as metal-organic frameworks (MOFs) and methods for their synthesis are provided herein. The MOFs include a $M_6(\mu_3\text{-OH})_8(OH)_8(\mu^2,\eta^2\text{-}(O_2C)_2\text{cyclam})_8$ cluster, and a metal atom coordinated to the one or more cyclam of the cluster, wherein M is Zr or Hf, and the metal atom is any one of Cu, Ni, Cr, Ru, Co, and Gd. The MOFs can be used as an adsorbent, alone or in a medium with other components, of $CO_2$. The MOFs can also be used as a catalyst for the transformation of $CO_2$ and epoxides to cyclic carbonates. The MOFs can also be used in the electrochemical catalytic reduction of $CO_2$. The MOFs can also be used for photocatalytic $CO_2$ reduction for the production of carbon-based fossil fuels. The MOFs can also be used for light-induced nitric oxide (NO) release. The MOFs can also be used as magnetic resonance imaging (MRI) agents.

19 Claims, 11 Drawing Sheets

METAL-ORGANIC FRAMEWORKS FOR THE ADSORPTION AND CATALYTIC TRANSFORMATIONS OF CARBON DIOXIDE

CROSS REFERENCE TO RELATED APPLICATION

This application claims the benefit of U.S. Provisional Application No. 62/719,944 filed Aug. 20, 2018, the entire contents of which is incorporated by reference herein.

STATEMENT REGARDING FEDERALLY SPONSORED RESEARCH OR DEVELOPMENT

This invention was made with Government support under Grant/Contract No. DE-SC0012446 awarded by the United States Department of Energy. The U.S. government may have certain rights in this invention.

FIELD OF THE INVENTION

The present invention relates to the synthesis of novel crystalline porous materials known as metal-organic frameworks (MOFs) and their use in transforming carbon dioxide ($CO_2$) into useful chemicals. More specifically, the present invention is directed to MOFs for use in various applications such as $CO_2$ adsorption, catalytic transformation of $CO_2$ and epoxides to cyclic carbonates, electrochemical catalytic reduction of $CO_2$, and photocatalytic $CO_2$ reduction for the production of carbon-based fossil fuels.

BACKGROUND OF THE DISCLOSURE

Metal-organic frameworks (MOFs) are compounds consisting of metal ions or clusters coordinated to organic ligands to form one-, two-, or three-dimensional structures. MOFs are composed of two major components: a metal ion or cluster of metal ions and an organic molecule called a linker. The organic units are typically mono-, di-, tri-, or tetravalent ligands. The choice of metal and linker dictates the structure and hence properties of the MOF. For example, the metal's coordination preference influences the size and shape of pores by dictating how many ligands can bind to the metal and in which orientation.

MOFs are often porous. In some cases, the pores are stable during elimination of the guest molecules (often solvents) and can be refilled with other compounds. Because of this property, MOFs are of interest for the storage of gases such as hydrogen and carbon dioxide. Other possible applications of MOFs are in gas purification, in gas separation, in catalysis, as sensors, and as supercapacitors.

Technologies that trap and/or chemically transform $CO_2$ to industrially useable products have received widespread attention in recent years, further encouraged by government and environmental policy aimed at addressing climate and renewable energy challenges.

DETAILED DESCRIPTION

Figure 1:
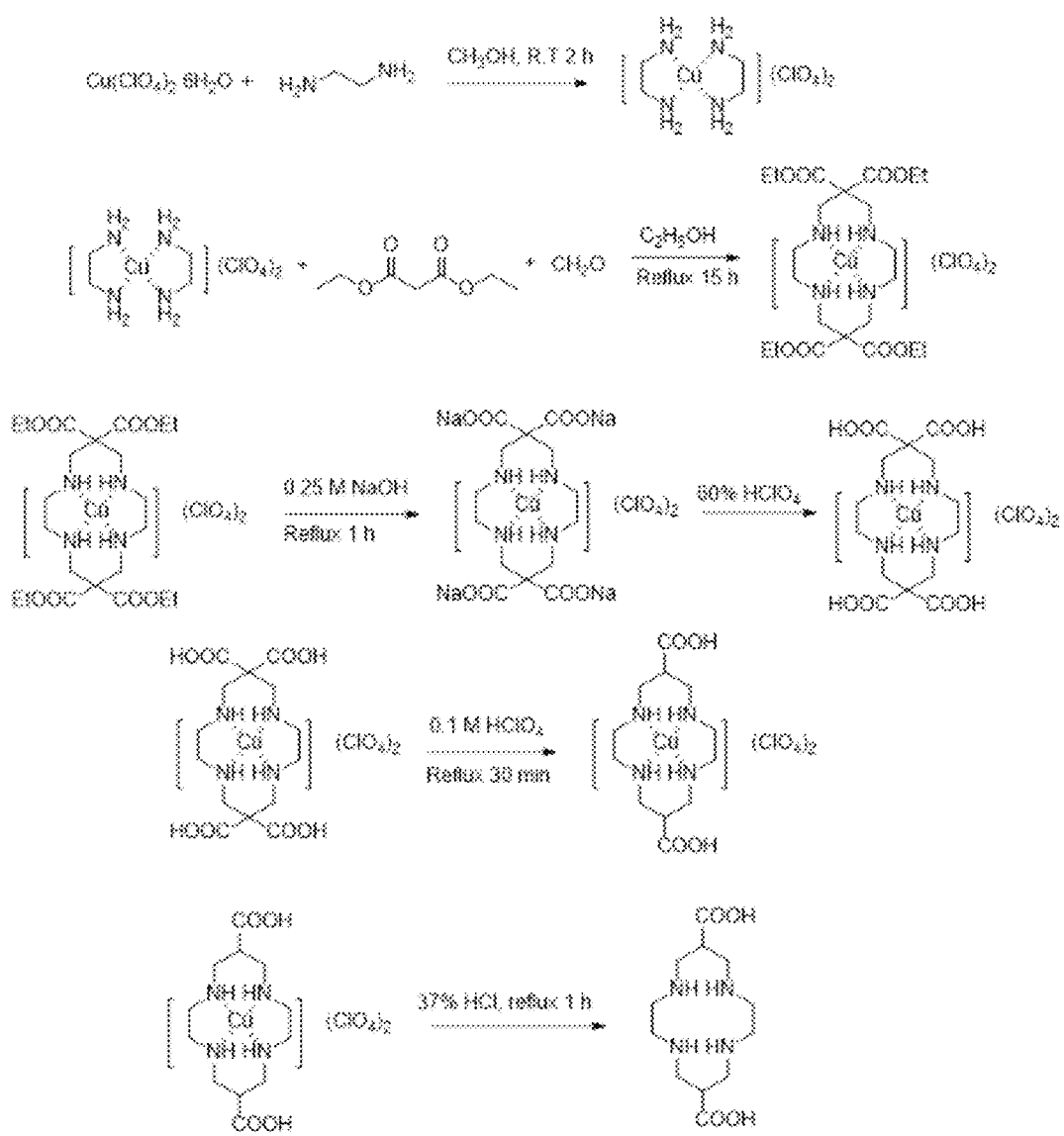
FIG. 1 is an illustration of a procedure for the synthesis of 6,13-dicarboxy-1,4,8,11-tetrazacyclotetradecane (chemical structure (1))

The following description of the embodiments is merely exemplary in nature and is in no way intended to limit the subject matter of the present disclosure, their application, or uses.

As used throughout, ranges are used as shorthand for describing each and every value that is within the range. Any value within the range can be selected as the terminus of the range. Unless otherwise specified, all percentages and amounts expressed herein and elsewhere in the specification should be understood to refer to percentages by weight.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent, alternatively ±5 percent, alternatively ±1 percent, alternatively ±0.5 percent, and alternatively ±0.1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

In accordance with various aspects of the present disclosure, novel crystalline porous materials known as metal-organic frameworks (MOFs) and methods for their synthesis are provided herein.

In some instances, MOFs produced in accordance with various aspects of the present disclosure can be used as an adsorbent, alone or in a medium with other components, of $CO_2$. In some instances, MOFs produced in accordance with various aspects of the present disclosure can be used as a catalyst for the transformation of $CO_2$ and epoxides to cyclic carbonates. In some instances, MOFs produced in accordance with various aspects of the present disclosure can be used in the electrochemical catalytic reduction of $CO_2$. In some instances, MOFs produced in accordance with various aspects of the present disclosure can be used for photocatalytic $CO_2$ reduction for the production of carbon-based fossil fuels. In some instances, MOFs produced in accordance with various aspects of the present disclosure can be used for light-induced nitric oxide (NO) release. In some instances, MOFs produced in accordance with various aspects of the present disclosure can be used as magnetic resonance imaging (MRI) agents.

MOFs produced in accordance with various aspect of the present disclosure can be described as being comprised of a plurality of metal cluster compounds. Adjacent metal cluster compounds are bound to each other via a bridging ligand or "linker". In some instances, the metal of the metal cluster compounds are zirconium. In other instances, the metal of the metal cluster compounds can be hafnium. In some instances, the bridging ligand has the following chemical structure (1):

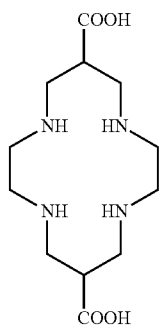

(1)

where each carboxylate group is bound to one or more metals in an individual metal cluster compound. The bridging ligand having chemical structure (1) can be described as having a cyclic group with multiple Lewis basis groups within the cycle (i.e., cyclam or 1,4,8,11-tetraazacyclotetradecane) and two linking metal binding groups (i.e., carboxylates) bound to the cyclic group. In some instances, the bridging ligand can have a cyclic group, with multiple Lewis basic groups, other than a cyclam. Also, in some instances other functional groups can be used instead of carboxylates for binding to one or more metals in an individual metal cluster compound.

In some instances, a metal atom can be chelated to the amines in chemical structure (1). In some instances, the metal atom is copper. In some instances, the metal atom is nickel. MOFs according to the present disclosure having copper or nickel may be particularly useful as $CO_2$ adsorbents, as catalysts for thermal, photochemical or electrochemical transformation of $CO_2$. In some instances, the metal atom is chromium. In some instances, the metal atom is ruthenium. MOFs according to the present disclosure having chromium or ruthenium may be particularly useful for light induced nitric oxide (NO) release, where a photo-triggered MOF system having NO donors can provide an excellent platform for the controlled release and delivery of pure NO. In some instances, the metal atom is cobalt. MOFs according to the present disclosure having cobalt may be particularly useful for photocatalytic reduction of $CO_2$. In some instances, the metal atom is gadolinium. MOFs according to the present disclosure having gadolinium may be particularly useful as MRI contrast agents.

In some instances, MOFs produced according to various aspects of the present disclosure crystallize in the space group I4/m. Each MOF node can be comprised of a $Zr_6(\mu_3\text{-}OH)_8(OH)_8(\mu^2,\eta^2\text{-}(O_2C)_2\text{cyclam})_8$ cluster ($Zr_6$-cluster) that is centered at I-lattice positions (i.e., unit cell origin and body center) with site symmetry $4/m$ ($D_{4h}$). Similar to other 8-connected $Zr_6$ clusters, the Zr-atoms of the $Zr_6$-cluster can occupy the corners of a distorted octahedron; each 8-coordinate $Zr^{4+}$ can have a distorted square antiprism geometry. The faces of the octahedron defined by the 6 Zr-atoms can be capped by $\mu_3$-OH groups that fill 4 coordination sites around each $Zr^{4+}$. In some instances, eight ligands, such as a ligand of chemical structure (1), are coordinated to each cluster with each carboxylate bridging between an axial $Zr^{4+}$ and equatorial $Zr^{4+}$ of $Zr_6$-octahedron. The coordination sphere around each equatorial Zr-atom can be completed by two terminal —OH groups.

Examples

Synthesis of Ligands

The 6,13-dicarboxy-1,4,8,11-tetrazacyclotetradecane)-copper (II) perchlorate [CuL(ClO$_4$)$_2$] and 6,13-dicarboxy-1,4,8,11-tetrazacyclotetradecane (L) ligands were synthesized based on previous reports with minor modifications. The cyclam-based ligands can be obtained using a 5 steps synthetic route starting from Cu(II) perchlorate and ethylene diamine (FIG. 1).

Synthesis of 6,13-dicarboxy-1,4,8,11-tetrazacyclotetradecane)-copper (II) Perchlorate [CuL(ClO$_4$)$_2$]

The Cu-based cyclam ligand [CuL(ClO$_4$)$_2$] was synthesized according to a literature procedure. In a typical synthesis, the tetracarboxylate precursor [Cu(tetacH$_4$)](ClO$_4$)$_2$ (630 mg, 0.99 mmol) was added to 10 mL of 0.1 M HClO$_4$ solution and heated at reflux for 1 h. After the reaction mixture cooled down to room temperature (R.T.), 3 mL of 60% $HClO_4$ was added and the solution refrigerated overnight. The product was filtered off as red crystalline solid (0.38 g, 46% yield). The phase purity of $CuL(ClO_4)_2$ was verified by powder X-ray diffraction (PXRD).

Synthesis of Free-Base Ligand
6,13-dicarboxy-1,4,8,11-tetrazacyclotetradecane
(Chemical Structure (1))

The free-base ligand was prepared by the demetallation of $CuL(ClO_4)_2$. The copper was removed by refluxing [CuL$(ClO_4)_2$] (0.32 g, 0.58 mmol) in 20 mL of 37% HCl for 1 h. The resultant white solid was filtered and washed with ethanol. After drying under vacuum, a white powder (0.16 g, 95% yield) was obtained. (ESI-MS: $[M-H]^+$ m/z=289.19; structure also confirmed via $^1H$ NMR, $^{13}C$ NMR and HSQC).

Synthesis of 6,13-dicarboxy-1,4,8,11-tetrazacyclo-tetradecane)-nickel (II) Perchlorate $[NiL(ClO_4)_2]$ $.2H_2O$ The Ni based cyclam ligand $[NiL(ClO_4)_2].2H_2O$ was synthesized under solvothermal conditions. In a 20 mL vial, $NiCl_2.6H_2O$ (70 mg, 0.295 mmol) and chemical structure (1) (70 mg, 0.242 mmol) were dissolved in 5 mL $H_2O$ with addition of 0.02 g NaOH (0.5 mmol). The vial was heated in a 100° C. oven for 6 h. After cooling to R.T., 2 mL of 60% $HClO_4$ was added and the solution refrigerated overnight. The product was filtered off as an orange crystalline solid: (38 mg, 26.9% yield). The phase purity of $[NiL(ClO_4)_2]$ $.2H_2O$ was verified by PXRD.

Synthesis of MOFs

Synthesis of VPI-100 (Cu)

Figure 2A:
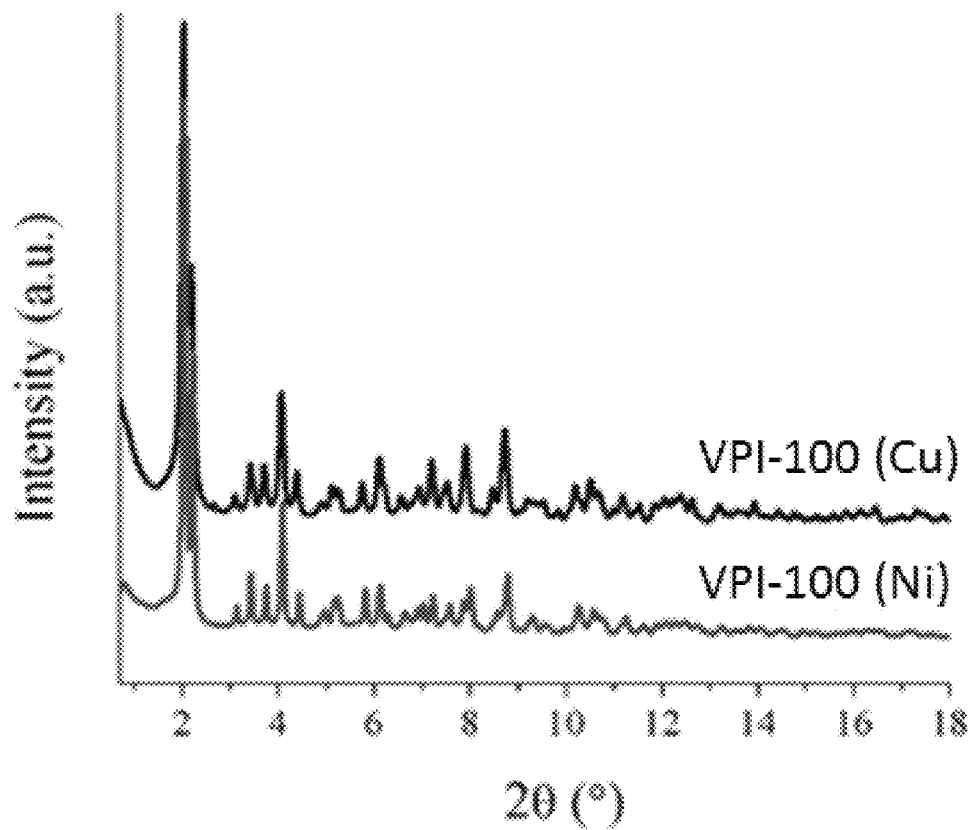
FIG. 2A is a graph of powder X-ray diffraction (PXRD) patterns, measured at room temperature using synchrotron X-ray diffraction, of two metal-organic frameworks (MOFs), VPI-100 (Cu) and VPI-100 (Ni), produced in accordance with various aspects of the present disclosure.

In an 8 mL vial, $ZrCl_4$ (14 mg, 0.06 mmol) was dissolved in 4 mL of dry N,N-dimethyl formamide (DMF) with 0.44 mL (200 eq.) of formic acid. The vial was heated in an 80° C. oven for 1 h. After cooling to R.T., $[CuL(ClO_4)_2]$ (L=chemical structure (1), 33 mg, 0.06 mmol) was added and the solution was sonicated for 10 min. Then, the mixture was heated in a 120° C. oven for 24 h. After cooling to R.T., the resultant solid was isolated by centrifugation, washed with fresh DMF (3×1 mL) and acetone (3×1 mL). The powder was dried under vacuum at 60° C. A violet crystalline powder was obtained (32 mg, 86% yield). The phase purity of VPI-100 (Cu) was verified by PXRD (FIG. 2A).

Synthesis of VPI-100 (Ni)

In an 8 mL vial, $ZrCl_4$ (14 mg, 0.06 mmol) was dissolved in 2 mL of dry DMF with 0.44 mL (200 eq.) of formic acid. In a separate vial, $NiCl_2.6H_2O$ (14 mg, 0.06 mmol) and free-base ligand (chemical structure (1), 17.3 mg, 0.06 mmol) were added to 2 mL of dry DMF, and sonicated for 10 mins. Then, both vials were heated in an 80° C. oven for 1 h. The solutions were combined into one vial and heated in a 120° C. oven for 24 h. After cooling to R.T., the resultant solid was isolated by centrifugation, washed with fresh DMF (3×1 mL), and acetone (3×1 mL). The product was dried under vacuum at 60° C. A light pink crystalline powder was obtained (22 mg, 60% yield). The phase purity of VPI-100 (Ni) was confirmed by PXRD (FIG. 2A).

Synthesis of VPI-100 (Co)

Figure 2B:
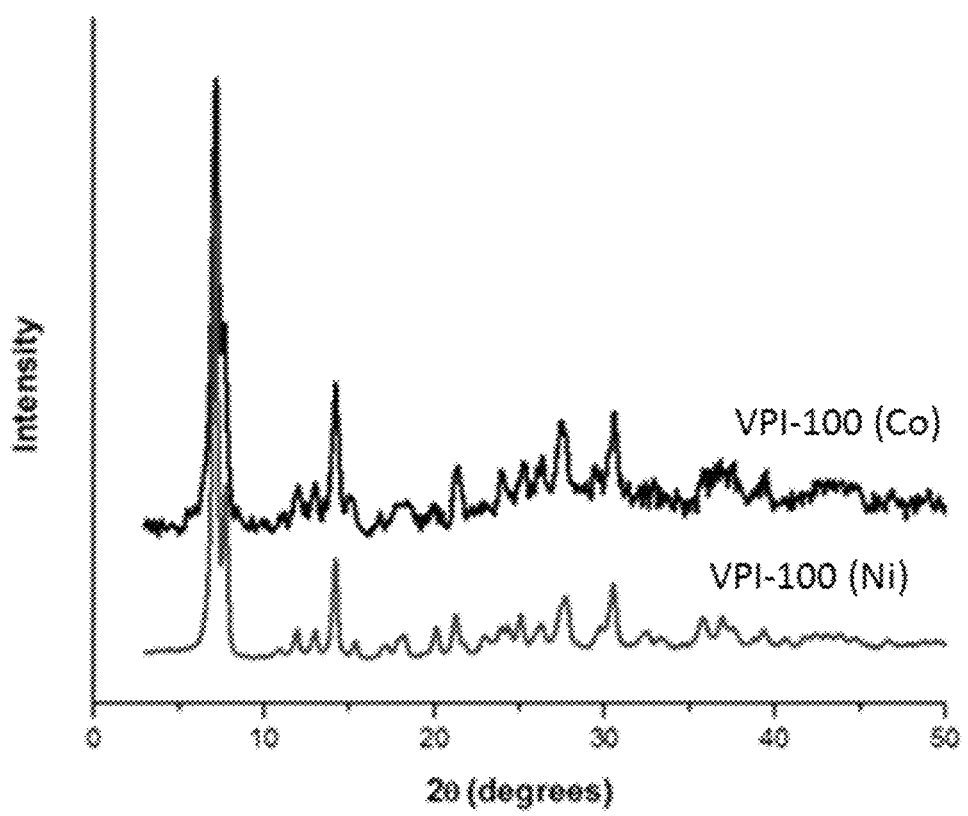
FIG. 2B is a graph of PXRD patterns, measured at room temperature using synchrotron X-ray diffraction, of two MOFs, VPI-100 (Co) and VPI-100 (Ni), produced in accordance with various aspects of the present disclosure.

In an 8 mL vial, $ZrCl_4$ (14 mg, 0.06 mmol) was dissolved in 2 mL of dry DMF with 0.44 mL (200 eq.) of formic acid. In a separate vial, $CoCl_2.6H_2O$ (14.3 mg, 0.06 mmol) and free-base ligand (chemical structure (1), 17.3 mg, 0.06 mmol) were added to 2 mL of dry DMF, and sonicated for 10 mins. Then, both vials were heated in an 80° C. oven for 1 h. The solutions were combined into one vial and heated in a 120° C. oven for 24 h. After cooling to R.T., the resultant solid was isolated by centrifugation, washed with fresh DMF (3×1 mL), and acetone (3×1 mL). The product was dried under vacuum at 60° C. A light green crystalline powder was obtained (22 mg, 60% yield). The phase purity of VPI-100 (Co) was confirmed by PXRD (FIG. 2B). Note: in some cases, bubble with O2 or air in the vial of $CoCl_2.6H_2O$ and free-base ligand before and after heat (80° C.) for 15 mins can improve the crystallinity of resultant powder if poor crystallinity was obtained.

In some instances, the synthetic protocols above can be modified. For example, in some instances, a different zirconium containing salt such as $ZrOCl_2$ can be used instead of $ZrCl_2$. In some instances, a hafnium containing salt such as $HfCl_4$ can be used instead of the zirconium-containing salt. With regard to VPI-100 (Cu), in some instances, a salt such as $CuLCl_2$ or a combination of $CuCl_2(PF_6)_2$ and the ligand in free-base form can be used instead of $CuL(ClO_4)_2$. With regard to VPI-100 (Ni), in some instances, a nickel salt such as $NiCl_2$, $Ni(OAc)_2$, of $Ni(NO_3)_2$ can be used instead of $NiCl_2.6H_2O$. With regard to VPI-100 (Co), in some instances, a cobalt salt such as $CoCl_2$, $Co(OAc)_2$, of $Co(NO_3)_2$ can be used instead of $CoCl_2.6H_2O$ In some instances, solvent other than DMF, such as, for example N,N-diethyl formamide (DEF) of dimethyl sulfoxide (DMSO) can be used. In the examples above, formic acid is used as a modulator to control the nucleation and crystallization rate of MOFs. In some instances, other acids such as, for example, acetic acid or propionic acid can be used instead of formic acid. Reaction temperatures and times can also be varied. In both examples above, oven heating occurs at 120° C. for 24 h. In some instances, this temperature can be varied between about 80-140° C. In some instances, the time can be as low as one hour.

Structure of Synthesized MOFs

Figure 3:
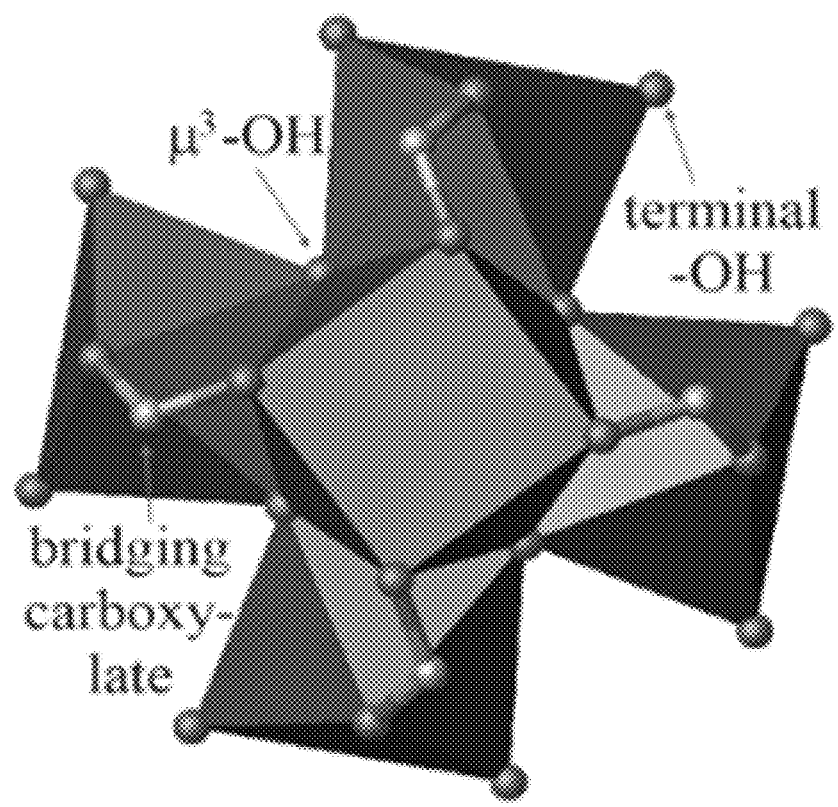
FIG. 3 is an illustration of a cluster of an MOF structure, VPI-100 (Cu), produced in accordance with various aspects of the present disclosure (disordered solvent, chloride, and H-atoms are omitted for clarity)
Figure 4:
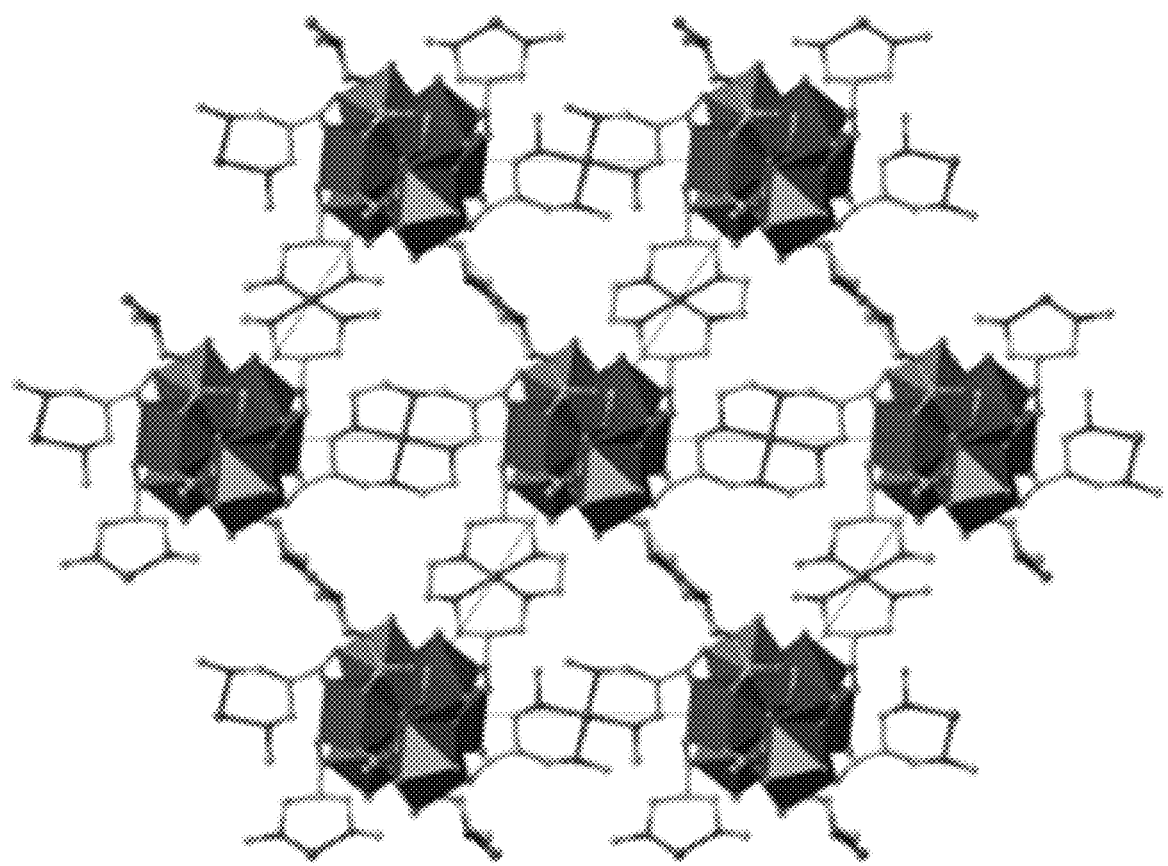
FIG. 4 is a polyhedral drawing of a $Zr_6(\mu_3\text{-OH})_8(OH)_8(\mu^2,\eta^2\text{-}(O_2C)_2cyclam)_8$ cluster an MOF structure, VPI-100 (Cu), produced in accordance with various aspects of the present disclosure, as viewed down [001] (i.e., the 4-fold axis)
Figure 5:
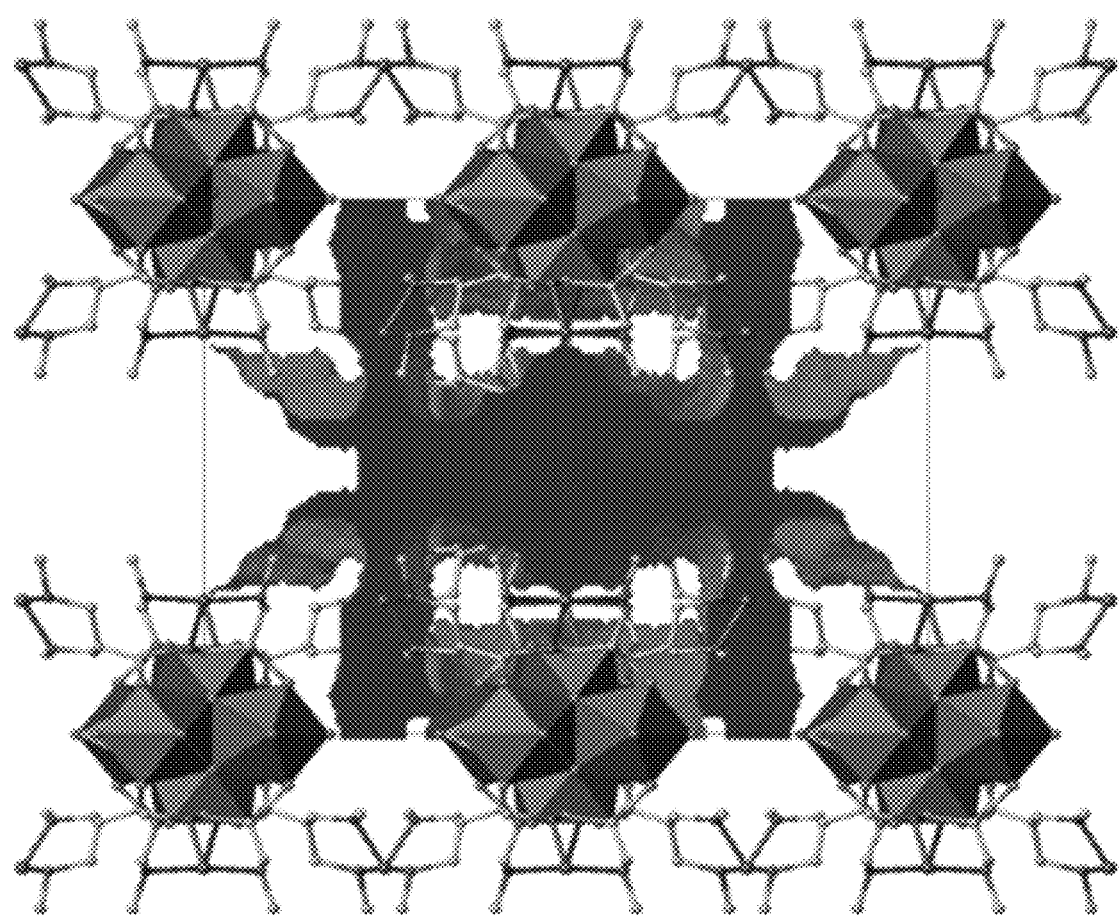
FIG. 5 is an illustrative view down [110] depicting the pore space in the MOF of FIG. 3.

As shown in FIGS. 3-5, VPI-100 (Cu) and VPI-100 (Ni) crystallize in the space group I4/m. FIG. 3 is a polyhedral drawing of the $Zr_6(\mu_3-OH)_8(OH)_8(\mu^2,\eta^2-(O_2C)_2cyclam)_8$ cluster as viewed down [001] (i.e. the 4-fold axis). FIG. 4 is a packing diagram viewed down [111] and depicting the cyclam linkers connecting the $Zr_6$-clusters along the cell body diagonals. Six of the eight closest $Zr_6$-clusters are depicted. The remaining two sit directly above and below the central $Zr_6$ cluster. FIG. 5 is a view down [110] depicting the pore space in the MOF. In FIGS. 3-5 the following color scheme is adopted: Zr, light blue; C, grey; O, red; N, blue; Cu, green. In the structural models, each MOF node is comprised of a $Zr_6(\mu_3-OH)_8(OH)_8(\mu^2,\eta^2-(O_2C)_2cyclam)_8$ cluster ($Zr_6$-cluster) that is centered at I-lattice positions (i.e. unit cell origin and body center) with site symmetry 4/m ($D_{4h}$). Similar to other 8-connected $Zr_6$ clusters in the art, the Zr-atoms of the $Zr_6$-cluster occupy the corners of a distorted octahedron; each 8-coordinate $Zr^{4+}$ has a distorted square antiprism geometry (FIG. 3). The faces of the octahedron defined by the six Zr-atoms are capped by $\mu_3$-OH groups that fill 4 coordination sites around each $Zr^{4+}$. Eight cyclam ligands are coordinated to each cluster with each carboxylate bridging between an axial $Zr^{4+}$ and equatorial $Zr^{4+}$ of Zr$_6$-octahedron. The coordination sphere around each equatorial Zr-atom is completed by two terminal —OH groups.

CO$_2$ Adsorption Uptake Studies

The CO$_2$ adsorption uptake of VPI-100-M is summarized in table 1. For the Cu analogue, the CO$_2$ adsorption capacity at 296 K and 1 atm was 3.76 wt % (19.15 cm$^3$/g at STP, 0.85 mmol/g), which increased to 6.65 wt % (33.85 cm$^3$/g at STP, 1.51 mmol/g) when the temperature was decreased to 273 K. For the Ni analogue, the CO$_2$ adsorption capacity at 296 K and 1 atm was 2.70 wt % (13.79 cm$^3$/g at STP, 0.62 mmol/g), which increased to 5.52 wt % (28.20 cm$^3$/g at STP, 1.26 mmol/g) when the temperature was decreased to 273 K. When the Ni analogue was activated at 120° C., the CO$_2$ uptake capacity improved significantly, leading to 9.87 wt % adsorption (50.23 cm$^3$/g at STP, 2.24 mmol/g) at 273 K and 1 atm.

TABLE 1

| MOF | Activation Temp. (° C.) | BET Surface Area (m$^2$/g) | CO$_2$ sorption at 273 K and 1 atm | | Q$_{st}$ (kJ/mol) |
| --- | --- | --- | --- | --- | --- |
| | | | STP (cm$^3$/g) | Wt % | |
| VPI-100 (Cu) | 100 | 398 | 33.85 | 6.65 | −38.4 |
| VPI-100 (Ni) | 100 | 344 | 28.20 | 5.52 | −36.4 |
| VPI-100 (Ni) | 120 | 612 | 50.23 | 9.83 | −31.2 |

Catalytic Experiments—Cyclic Carbonate Formation

In a typical catalysis experiment as illustrated in reaction scheme (1), VPI-100 (0.008 mmol), tetrabutylammonium bromide (TBAB, 99 mg, 0.31 mmol), and epoxide (31.3 mmol) were added to an autoclave reactor.

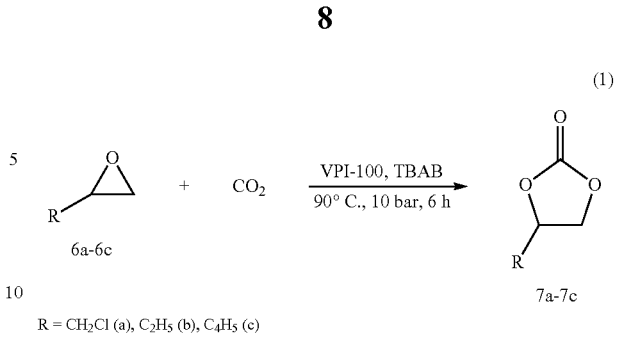

(1)

R = CH$_2$Cl (a), C$_2$H$_5$ (b), C$_4$H$_5$ (c)

Figure 6:
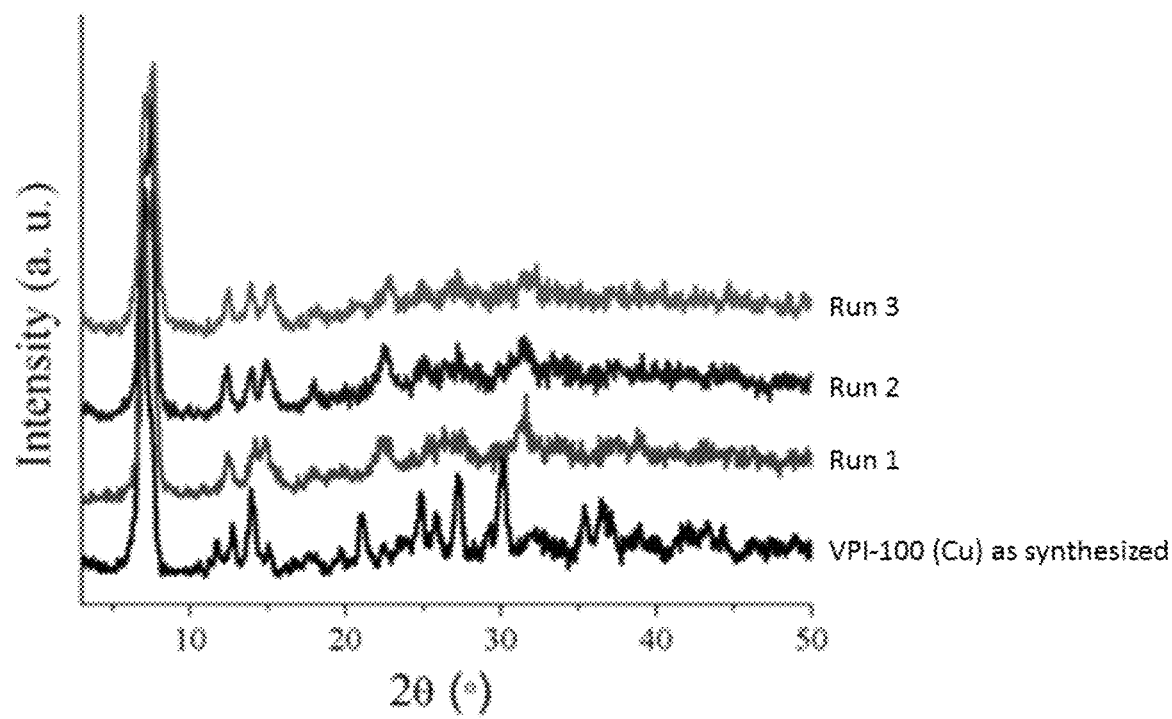
FIG. 6 is a graph of PXRD patterns of VPI-100 (Cu) as synthesized and after each of three consecutive uses as a catalyst.
Figure 7:
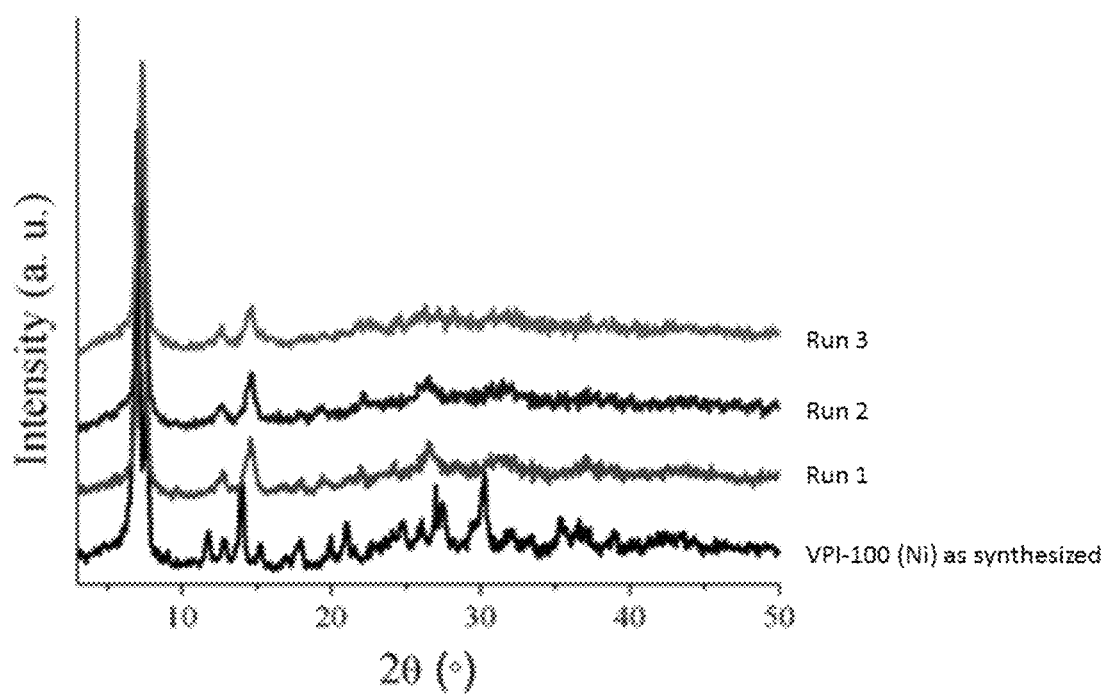
FIG. 7 is a graph of PXRD patterns of VPI-100 (Ni) as synthesized and after each of three consecutive uses as a catalyst.

Catalytic reactions were carried out at 90° C. and 10 bar of CO$_2$ for 6 h, and the resulting mixtures were analyzed by $^1$H NMR to determine the yield and the purity of cycloaddition products. The catalytic activities of VPI-100 MOFs are shown in Table 2. In Table 2, below conversion % was evaluated from the $^1$H NMR spectra by integration of epoxide versus cyclic carbonate peaks, turnover number was determined by calculating [product (mmol)/active site (mmol)], where "active site" is the sum of both the unsaturated Zr and Cu/Ni metal centers, and turnover frequency was determined using [TON/time (h)] (R$_1$, R$_2$ and R$_3$ stand for 3 cycles for using same VPI-100 MOF materials as catalyst). As can be seen, the reaction yields for cycloaddition of CO$_2$ with epichlorohydrin (6a) catalyzed by VPI-100 (Cu) and VPI-100 (Ni) are 94.3 (±0.6) % and 97 (±1) %, respectively. Furthermore, the corresponding turnover frequency (TOF) values of VPI-100 (Cu) and VPI-100 (Ni) are 72.3±0.6 and 75±1 h$^{-1}$, respectively, are among the highest of the previously reported values for MOFs. Furthermore, the VPI-100 MOFs were easily recovered from the reaction mixture by centrifugation and reused for at least 3 cycles without substantial loss of catalytic activity. Although the overall quality of powder patterns has decreased with the noticeable broadening of the peaks, the MOFs largely retained their crystallinity after the catalytic cycles of forming product 7a from CO$_2$ and epoxide 6a (for VPI-100 (Cu), see FIG. 6; for VPI-100 (Ni), see FIG. 7).

TABLE 2

| | | | | Conversion (%) | | | TON | | | TOF (h$^{-1}$) | | |
| --- | --- | --- | --- | --- | --- | --- | --- | --- | --- | --- | --- | --- |
| Entry | Epoxide | Product | Catalyst | R1 | R2 | R3 | R1 | R2 | R3 | R1 | R2 | R3 |
| 1 | (6a) | (7a) | VPI-100 (Cu), TBAB | 94 | 95 | 94 | 431 | 439 | 431 | 72 | 73 | 72 |
| 2 | (6a) | (7a) | VPI-100 (Ni), TBAB | 96 | 98 | 98 | 443 | 452 | 453 | 74 | 75 | 76 |
| 3 | (6b) | (7b) | VPI-100 (Cu), TBAB | 60 | 52 | 40 | 273 | 236 | 185 | 46 | 39 | 31 |
| 4 | (6b) | (7b) | VPI-100 (Ni), TBAB | 50 | 50 | 43 | 229 | 229 | 199 | 38 | 38 | 33 |

TABLE 2-continued

| Entry | Epoxide | Product | Catalyst | Conversion (%) R1 | R2 | R3 | TON R1 | R2 | R3 | TOF (h⁻¹) R1 | R2 | R3 |
|---|---|---|---|---|---|---|---|---|---|---|---|---|
| 5 | (6c) | (7c) | VPI-100 (Cu), TBAB | 13 | 16 | 18 | 60 | 76 | 81 | 10 | 13 | 14 |
| 6 | | | VPI-100 (Ni), TBAB | 18 | 20 | 17 | 85 | 92 | 78 | 14 | 15 | 13 |

Catalytic Experiments—Electrochemical $CO_2$ Reduction

Figure 8:
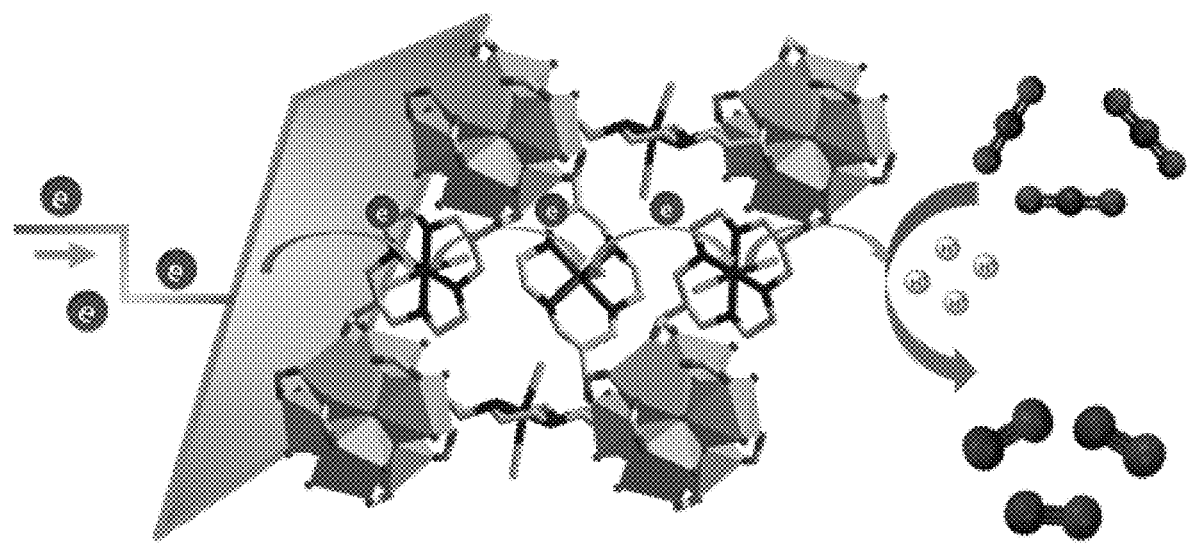
FIG. 8 is a schematic illustration of a system electrochemical reduction of $CO_2$ to CO using VPI-100 (Ni) as a catalyst.

MOFs produced in accordance with various aspects of the present disclosure may also be used can also be used as catalyst for electrochemical reduction of $CO_2$. FIG. 8 is a schematic illustration of a system electrochemical reduction of $CO_2$ to CO using VPI-100 (Ni). In FIG. 8, VPI-100 (Ni) is integrated with a conductive substrate to achieve a functional $CO_2$ electrochemical reduction system. In some instances, the conductive substrate is a fluorine-doped tin oxide (FTO). In other instances, the conductive substrate and be any one of an indium tin oxide (ITO), an indium-doped zinc oxide (IZO), an aluminum-doped zinc oxide (AZO), a gallium-doped zinc oxide (GZO), an indium-doped cadmium oxide (ICO), a carbon nanotube (CNT) film, or an inherently conductive polymer (ICP such as polyaniline, poly(3,4-ethylenedioxythiophene) (PEDOT), poly(3,4-ethylenedioxythiophene): poly(styrene sulfonate) (PEDOT: PSS), poly(4,4-dioctyl cyclopentadithiophene) doped with iodine or 2,3-dichloro-5,6-dicyano-1,4-benzoquinone (DDQ).

Figure 9:
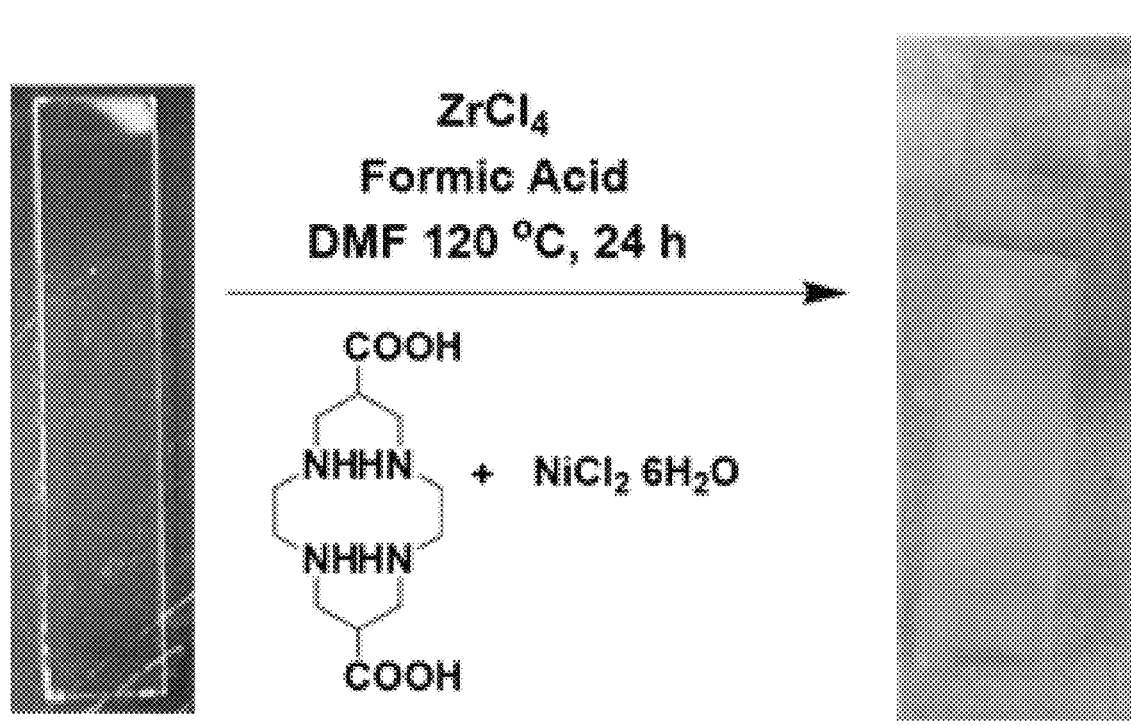
FIG. 9 is a schematic illustration of the fabrication of an electrochemical $CO_2$ reduction system.
Figure 10:
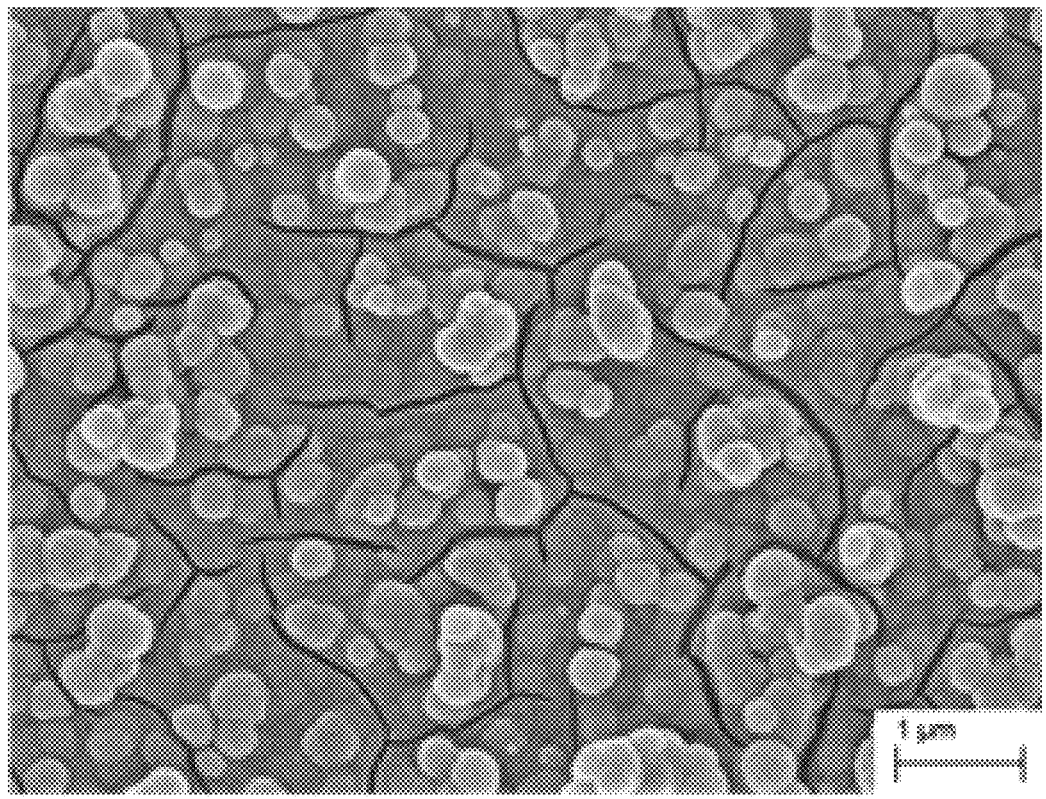
FIG. 10 is a scanning electron microscope (SEM) image showing a thin film of VPI-100 (Ni) MOF powders on the FTO substrate of FIG. 9.

FIG. 9 is a schematic illustration showing the fabrication of an electrochemical $CO_2$ reduction system. In FIG. 9, VPI-100 (Ni) is synthesized as described above and coated as a thin film on an FTO substrate. FIG. 10 is a scanning electron microscope (SEM) image showing a thin film of VPI-100 (Ni) MOF clusters on the FTO substrate of FIG. 9.

Figure 11:
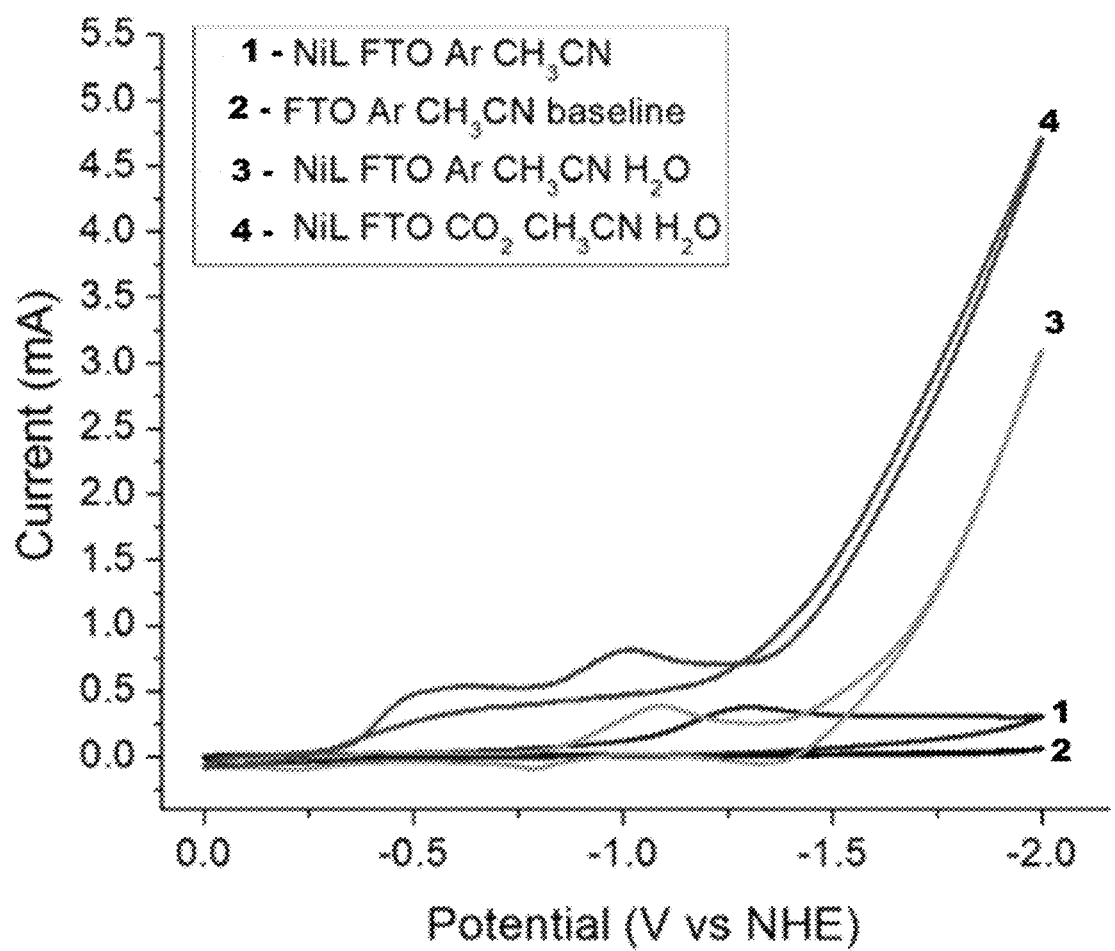
FIG. 11 is a graph illustrating cyclic voltammetry measurements for NiL complexes in $CH_3CN$ and $CH_3CN/H_2O$ (v/v 4:1), 0.1 M $TBAPF_6$, (reference electrode: $Ag/AgNO_3$, counter electrode: Pt, and working electrode: FTO)
Figure 12:
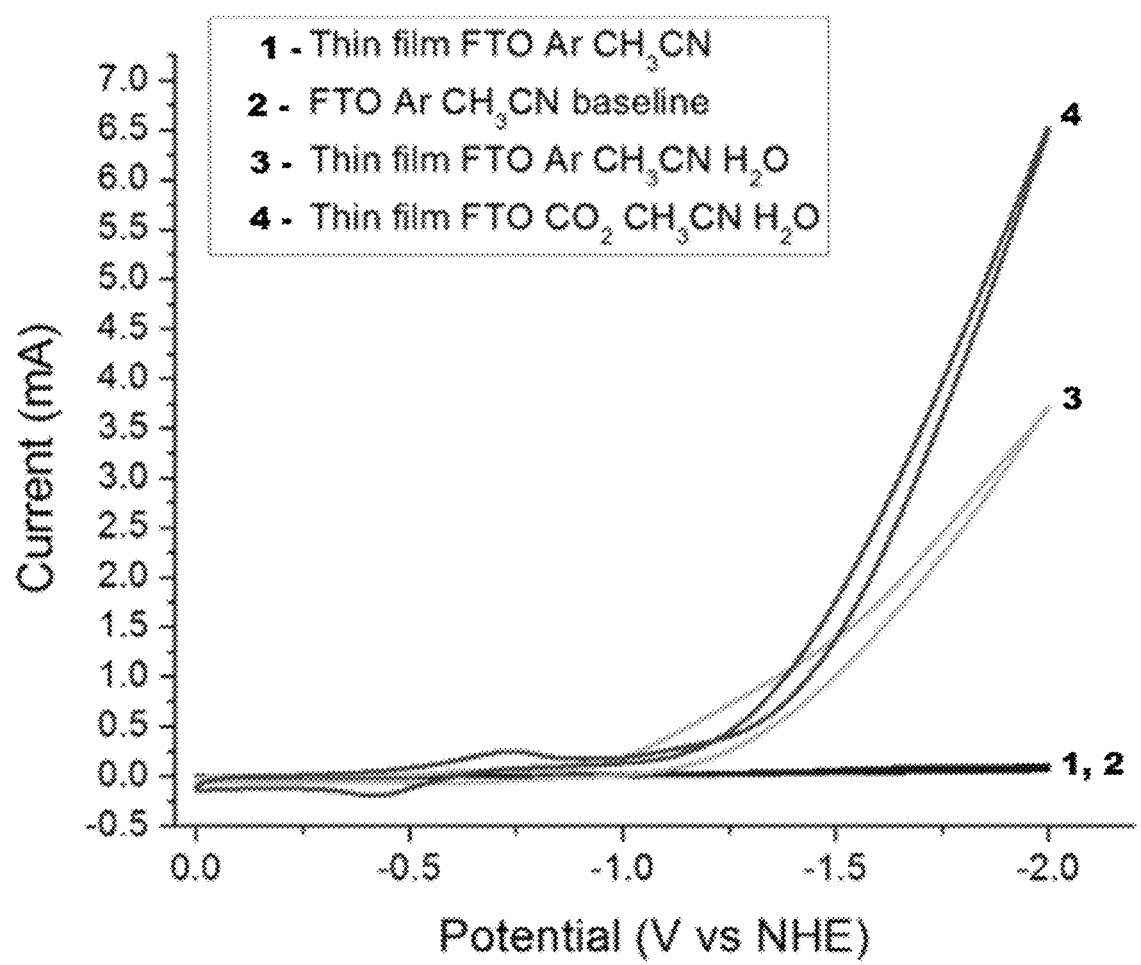
FIG. 12 is a graph illustrating cyclic voltammetry measurements for a VPI-100-Ni MOF thin film in $CH_3CN$ and $CH_3CN/H_2O$ (v/v 4:1), 0.1 M $TBAPF_6$ (reference electrode: $Ag/AgNO_3$, counter electrode: Pt, and working electrode: FTO).

Cyclic voltammetry (CV) measurements of the synthesized NiL (L=chemical structure (1)) complexes and VPI-100-Ni MOFs under an argon or carbon dioxide environment were used to screen the MOF catalytic performance. FIG. 11 is a graph illustrating cyclic voltammetry measurements for NiL complexes in $CH_3CN$ and $CH_3CN/H_2O$ (v/v 4:1), 0.1 M $TBAPF_6$, (reference electrode: $Ag/AgNO_3$, counter electrode: Pt, and working electrode: FTO). FIG. 12 is a graph illustrating cyclic voltammetry measurements for a VPI-100-Ni MOF thin film in $CH_3CN$ and $CH_3CN/H_2O$ (v/v 4:1), 0.1 M $TBAPF_6$ (reference electrode: $Ag/AgNO_3$, counter electrode: Pt, and working electrode: FTO). The $Ni^{(II)(I)}$ reduction peak has been observed either in NiL and VPI-100-Ni thin film. For NiL, with the presence of $CO_2$, the Ni(II) to (I) redox couple becomes more irreversible and the reduction peak is shifted positively by 120 mV. A second reduction couple, which was attributed to Ni(I) to Ni(0) process has appeared. For both NiL and VPI-100-Ni thin film, significant catalytic current has been observed after the addition of $CO_2$, which is due to $CO_2$ reduction.

STATEMENTS OF THE DISCLOSURE

Statements of the Disclosure include:

Statement 1: A metal-organic framework (MOF), the MOF comprising a $M_6(\mu_3\text{-}OH)_8(OH)_8(\mu^2,\eta^2(O_2C)_2$cyclam$)_8$ cluster; and a metal atom coordinated to the one or more cyclam of the cluster, wherein M is Zr or Hf, and the metal atom is any one of Cu, Ni, Cr, Ru, Co, and Gd.

Statement 2: An MOF according to Statement 1, wherein M is Zr.

Statement 3: An MOF according to Statement 1 or 2, wherein the metal atom is Cu, Ni or Co.

Statement 4: An MOF according to Statement 1 or 2, wherein the metal atom is Cu or Ni.

Statement 5: An MOF according to Statement 1 or 2, wherein the metal atom is Cr or Ru.

Statement 6: An MOF according to Statement 1 or 2, wherein the metal atom is Co.

Statement 7: An MOF according to Statement 1 or 2, wherein the metal atom is Gd.

Statement 8: An MOF according to any one of Statements 1-7, wherein the MOF has a BET surface area of about 340 to about 620 $m^2/g$.

Statement 9: An MOF according to any one of Statements 1-8, wherein the MOF has a crystal structure characterized by a I4/m space group.

Statement 10: An electrochemical $CO_2$ reduction system, the system comprising a conductive substrate; and a film coated of a surface of the conductive substrate, the film comprising a MOF according to any one of Statements 1-9.

Statement 11: A $CO_2$ adsorbent medium, the medium comprising an MOF according to any one of Statements 1-9.

Statement 12: A method for removing $CO_2$ from a mixture of gases, the method comprising reacting the mixture of gases with an adsorbent medium according to Statement 11.

Statement 13: A method according to Statement 12, wherein the temperature of the mixture of gases is between about 273 K and about 296 K.

Statement 14: A method according to Statement 12 or 13, wherein the pressure of the mixture of gases is about 1 atm.

Statement 15: A method of synthesizing a cyclic carbonate, the method comprising reacting $CO_2$ and an epoxide in the presence of a catalyst, wherein the catalyst is a MOF according to any one of Statement 1-9.

Statement 16: A method according to Statement 15, further comprising recovering the catalyst after cyclic carbonate synthesis is complete.

Statement 17: A method according to Statement 16, further comprising reusing the recovered catalyst in a subsequent cyclic carbonate synthesis procedure.

Statement 18: A magnetic resonance imaging (MRI) contrast agent, the MRI contrast agent comprising an MOF according to any one of Statements 1-9.

Although the present invention and its objects, features and advantages have been described in detail, other embodiments are encompassed by the invention. All references cited herein are incorporate by reference in their entireties. Finally, those skilled in the art should appreciate that they can readily use the disclosed conception and specific embodiments as a basis for designing or modifying other structures for carrying out the same purposes of the present invention without departing from the scope of the invention as defined by the appended claims.

What is claimed is:

1. A metal-organic framework (MOF), the MOF comprising:
   a $M_6(\mu_3\text{-}OH)_8(OH)_8(\mu_2,\eta_2\text{-}(O_2C)_2\text{cyclam})_8$ cluster; and
   a metal atom coordinated to the one or more cyclam of the cluster,
   wherein
   M is Zr or Hf, and
   the metal atom is any one of Cu, Ni, Cr, Ru, Co, and Gd.

2. The MOF of claim 1, wherein M is Zr.

3. The MOF of claim 2, wherein the metal atom is Cu, Ni or Co.

4. The MOF of claim 2, wherein the metal atom is Cu or Ni.

5. The MOF of claim 2, wherein the metal atom is Cr or Ru.

6. The MOF of claim 2, wherein the metal atom is Co.

7. The MOF of claim 2, wherein the metal atom is Gd.

8. The MOF of claim 1, wherein the MOF has a BET surface area of about 340 to about 620 $m^2/g$.

9. The MOF of claim 1, wherein the MOF has a crystal structure characterized by a I4/m space group.

10. An electrochemical $CO_2$ reduction system, the system comprising:
    a conductive substrate; and
    a film coated on a surface of the conductive substrate, the film comprising an MOF according to claim 1.

11. A $CO_2$ adsorbent medium, the medium comprising an MOF according to claim 1.

12. A method for removing $CO_2$ from a mixture of gases, the method comprising reacting the mixture of gases with an adsorbent medium according to claim 11.

13. The method of claim 12, wherein the temperature of the mixture of gases is between about 273 K and about 296 K.

14. The method of claim 12, wherein the pressure of the mixture of gases is about 1 atm.

15. A method of synthesizing a cyclic carbonate, the method comprising:
    reacting $CO_2$ and an epoxide in the presence of a catalyst, wherein the catalyst is a MOF according to claim 1.

16. The method of claim 15, further comprising recovering the catalyst after cyclic carbonate synthesis is complete.

17. The method of claim 16, further comprising reusing the recovered catalyst in a subsequent cyclic carbonate synthesis procedure.

18. A magnetic resonance imaging (MRI) contrast agent, the MRI contrast agent comprising an MOF according to claim 1.

19. The MRI contrast agent of claim 18, wherein M is Zr and the metal atom is Gd.

* * * * *